United States Patent [19]

Mattern et al.

[11] Patent Number: 5,591,732
[45] Date of Patent: Jan. 7, 1997

[54] MEDICAMENT FOR INFLUENCING THE DEGREE OF ACTIVATION OF THE CENTRAL NERVOUS SYSTEM

[76] Inventors: Claudia Mattern, Enzianstrasse 4a, Starnberg D-82319; Rudiger Hacker, Ladestrasse 2, Herrsching D-82211, both of Germany

[21] Appl. No.: 185,832
[22] PCT Filed: May 28, 1993
[86] PCT No.: PCT/DE93/00473
§ 371 Date: Jun. 17, 1994
§ 102(e) Date: Jun. 17, 1994
[87] PCT Pub. No.: WO93/24128
PCT Pub. Date: Dec. 9, 1993

[30] Foreign Application Priority Data

Jun. 3, 1992 [DE] Germany .................. 42 18 292.1

[51] Int. Cl.$^6$ ..................... A61K 31/56; A61K 31/68
[52] U.S. Cl. ............................. 514/170; 514/178
[58] Field of Search ........................ 514/170, 178

[56] References Cited

U.S. PATENT DOCUMENTS

| | | | |
|---|---|---|---|
| 3,908,007 | 9/1975 | Itil et al. ................................ | 514/178 |
| 4,812,457 | 3/1989 | Narumiya et al. ..................... | 514/170 |
| 4,898,857 | 2/1990 | Aroonsakul ........................... | 514/171 |
| 4,902,680 | 2/1990 | Aroonsakul ........................... | 514/170 |
| 5,120,723 | 6/1992 | Gee et al. .............................. | 514/176 |
| 5,183,815 | 2/1993 | Saari et al. ............................. | 514/172 |
| 5,208,227 | 5/1993 | Gee et al. .............................. | 514/172 |

OTHER PUBLICATIONS

Dimpfel, W. and Hofman, H.-C., "Central Nervous System Monitoring; Reduction of Information Content of Quantitative Electroencephalograms for Continuous On–Line Display During Anesthesia", J. Schulte am Esch, E. Kochs (Eds.), Central Nervous System Monitoring in Anesthesia and Intensive Care 103–111 (1994).

Schober, F. and Dimpfel, W., "Relation between psychometric tests and quantitative topographic EEG in pharmacology", Int. J. Clinical Pharmacology, Therapy and Toxicology, vol. 30, No. 11, 428–430 (1992).

Trimmel, Michael, "Event–related potentials (ERPs) of the brain influenced by preceding slow potential shifts (pSPSs)", Journal of Psychophysiology 2:99–108 (1988).

Trimmel, Michael et al., "Occurrence of infraslow potential oscillations in relation to task, ability to concentrate and intelligence", Int. J. Psychophysiology 9:167–170 (1990).

Haase, H. and Kammel, W., "The Visual Stress Model—A Psychophysiological Method for the Evaluation of Operational Reliability of Pilots and Cosmonauts (Preprint)", 36th Congress of the International Astronautical Federation, Stockholm, Sweden, Oct. 7–12, 1985.

Morgan, W. P., EdD, FACSM, et al., "Psychological Monitoring of Overtraining and Staleness", Brit. J. Sports Med. 21(3):107–114 (1987).

*Primary Examiner*—Marianne M. Cintins
*Assistant Examiner*—Keith MacMillan
*Attorney, Agent, or Firm*—Merchant, Gould, Smith, Edell, Welter & Schmidt, P.A.

[57] ABSTRACT

Use of a medicament with a content of metanolone and/or Oral Turinabol for increasing and optimizing the degree of activation of the central nervous system and/or for prophylaxis and therapy of osteoporosis.

4 Claims, No Drawings

MEDICAMENT FOR INFLUENCING THE DEGREE OF ACTIVATION OF THE CENTRAL NERVOUS SYSTEM

This application is a 371 of PCT DE 93/00473, filed May 28, 1993.

The invention relates to a medicanent which, apart from its already known action in the metabolism, is able to positively influence the activation state of the central nervous system or physiologically optimize the same and/or is active in the prophylaxis and therapy of osteoporosis.

Apart from other factors, the psychophysiological and psychic capacity of the human being is significantly determined by the state of activation of the central nervous system. This activation can be evaluated by means of the shift of the average alpha-frequency in the electroencephalogram. Each physical or psychic stress to the human being leads to an increase of approximately 4 to 6 Hertz of the frequency as compared with the individual starting value. This increase is linked with an improvement to the psychophysiological capacity. If the stressing is excessive or cannot be adequately controlled, the alpha-frequency decreases after passing through an optimum. As a result the psychophysiological capacity drops and can sink below the starting value prior to the start of stressing.

Research carried out on top sportsmen proved that the increase of the alpha-frequency is triggered by mental concentration connected with completing the task. An appropriate physical activity before controlling the actual stress has the same effect. If the optimum of the activation is exceeded by false preparation, overstressing, fear situations or disturbing external influences, the capacity decreases, errors increase, corrections are associated with more psychic and physical effort. The degree of exhaustion on completing the task is higher.

In middle and old age a cause of the decreasing capacity is an inadequate stress activation of the central nervous system. In phases of longer-term and high psychophysiological stressing and particularly with restricted activation, the setting and maintaining of an optimum activation state of the central nervous system acquires particular significance at this age for maintaining and optimizing capacity.

Through changes in the hormonal balance as from an age of 45 to 50 years there can be a catabolic situation in the calcium metabolism of the bone, which leads to calcium depletion (osteoporosis). A substitution of this function without disturbing the endogenic control system is necessary. For woman in the menopause therapeutical schemes have been tested, but there is no satisfactory solution for men. All the steroid hormones and derivatives tested up to now have revealed clear negative influencing of the endogenic control system.

It has now surprisingly been found that both an optimum activation state of the central nervous system and also (simultaneously or separately therefrom) an activity during prophylaxis and therapy of osteoporosis can be obtained by the application of a medicament having a content of mestanolone and/or Oral-Turinabol.

The medicament can be used as a controlled-release dragee, depot form or buccal tablet, or in the form of a galenic formulation, which permits pernasal application by means of a nasal spray. Preference is given to a content of mestanolone and/or Oral-Turinabol of 5 to 20 mg per ingestion unit.

Mestanolone (STS 646, 17β-hydroxy-17-methyl-5αandrostan-3-one) is a testosterone derivative. As a result of the chemical modification the prevailing androgenic activity of the active ingredient is reduced and the anabolic activity increased. Mestanolone is authorized in Greece under the indication "anabolic/androgen".

It has surprisingly been found that, compared with other anabolically acting steroids (e.g. methandrostenolone), which can be therapeutically used, the anabolic activity of mestanolone is much lower. When administering the same dose (e.g. 10 to 20 mg daily) under mestanolone there is a reduction of the urea concentration in the blood and at 4% it is much lower than with the other steroids (up to 30%).

Research carried out on physically highly stressed test persons revealed that on supplying mestanolone the protein metabolism remains in equilibrium and neither during, not after stressing catabolic situations occur. However, a marked accentuation of the anabolic situation was not detected.

This research completely unexpectedly and surprisingly discovered a hitherto unknown further action of mestanolone, namely the supply thereof led to an optimization of the central nervous activation during preparation for the task and to a maintaining of this optimum activation even under high stresses. Thus, there was an increases psychophysiological capacity.

54 test persons highly stressed for a long period of time had, after the administration of 10 mg of mestanolone daily, a marked increase of the alpha-frequency by up to 4 Hertz. With this was associated a regularizing and optimizing of the frequency rise under stress. The test persons performed difficult exercises requiring high physical capacities linked with high intellectual concentration and muscular coordination with far fewer errors. Complicated movement sequences with a high degree of stressing did not lead to a reduction in the degree of activation and instead the increased capacity remained after several repeats.

Therefore the supply of mestanolone is suitable in high stress phases and particularly in human beings in middle and old age with activation deficiencies is able to trigger and support stress-adequate optimization of the central nervous activation state.

Due to these results comparative tests were carried out on 10 test persons, which were subject to exhausting physical stresses for 4 to 6 hours daily. Five of the test persons were given for six weeks on a daily basis between 5 and 10 mg of Oral-Turinabol, in order to ensure an adequate restoration and stressability. The other five test persons were given a placebo. The anabolic action of the medication was, as expected, detectable by means of the concentration of myoalbumin and urea in the serum. However, compared with the test persons who received the placebo, there was surprisingly also a clear increase of the central nervous activation of most of the test persons treated with Oral-Turinabol. This side effect of Oral-Turinabol was not hitherto known.

The application of the active substance can take place in the form of delayed-action dragees, depot forms or buccal tablets. However, it is particularly advantageous for a pernasal application of the medicanent in the form of a nasal spray. It would appear that this pernasal application facilitates passage through the blood-brain barrier. Therefore the active ingredient passes more rapidly and bypassing the first-pass metabolism in the liver to the effector organ, or organ, the steroid receptors present in the central nervous system. Associated with this bypassing action the necessary dose per individual application can be reduced to approximately 5 rag. By reducing the dose and bypassing the liver negative influences on the liver metabolism which, according to the literature could be caused by 17-alpha-methylation, are avoided.

A further, particularly advantageous characteristic of the further medical indication of mestanolone and Oral-Turinabol according to the invention is that these substances, unlike other anabolically active steroids, even in the case of administration over a longer period of time (20 mg daily for six weeks) have no negative reactions on the endogenic regulation of the testosterone level. This is also a surprising observation in view of the known behaviour of other anabolics.

The supply of mestanolone and/or Oral-Turinabol leads to an optimization of the central nervous activation without any negative influencing of the endogenic regulation of the testosterone level and therefore the individual anabolic/catabolic equilibrium in the metabolism. In addition, these substances offer the advantage of a mild anabolic action and therefore of favouring the calcium incorporation into the bone without disturbing the endogenic regulation. This makes it possible to use the stabilizing action on the metabolism also for the prophylaxis and therapy of osteoporosis. It is particularly important that a long-term application is possible without any harmful reactions. The above-described positive effect on the central nervous system has an additional advantageous action. However, naturally both effects can be individually used.

The features of the invention described in the description and in the claims can be essential both individually and in random combinations for the realization of the different embodiments of the invention.

We claim:

1. A method of increasing psychophysiological capacity in a human by optimizing the degree of activation of the central nervous system, said method comprising a step of:

(a) administering to the human a medicament containing a therapeutically effective amount of mestanolone, 4-chloro-1-dehydromethyltestosterone, or a mixture thereof.

2. The method of claim 1 wherein the medicament is a delayed-action dragee, a depot form or a buccal tablet.

3. The method of claim wherein the medicament is a formulation which permits pernasal application by nasal spray.

4. The method of claim 1 wherein the medicament includes 5 to 20 mg per ingestion unit of mestanolone, 4-chloro-1-dehydromethyltestosterone, or a mixture thereof.

* * * * *